United States Patent
Blomström et al.

(10) Patent No.: US 11,000,431 B2
(45) Date of Patent: May 11, 2021

(54) ABSORBENT ARTICLE AND METHOD FOR MANUFACTURING AN ABSORBENT ARTICLE

(71) Applicant: Essity Hygiene and Health Aktiebolag, Gothenburg (SE)

(72) Inventors: Philip Blomström, Gothenburg (SE); Peter Rönnberg, Gothenburg (SE)

(73) Assignee: Essity Hygiene and Health Aktiebolag, Gothenburg (SE)

(*) Notice: Subject to any disclaimer, the term of this patent is extended or adjusted under 35 U.S.C. 154(b) by 0 days.

(21) Appl. No.: 16/626,949

(22) PCT Filed: Jul. 5, 2018

(86) PCT No.: PCT/EP2018/068233
§ 371 (c)(1),
(2) Date: Dec. 27, 2019

(87) PCT Pub. No.: WO2019/008091
PCT Pub. Date: Jan. 10, 2019

(65) Prior Publication Data
US 2020/0129347 A1 Apr. 30, 2020

(30) Foreign Application Priority Data

Jul. 7, 2017 (WO) .............. PCT/EP2017/067068
Jul. 7, 2017 (WO) .............. PCT/EP2017/067071

(51) Int. Cl.
*A61F 13/476* (2006.01)
*A61F 13/56* (2006.01)
(Continued)

(52) U.S. Cl.
CPC .... *A61F 13/5616* (2013.01); *A61F 13/15577* (2013.01); *A61F 13/15634* (2013.01);
(Continued)

(58) Field of Classification Search
CPC ............... A61F 13/47; A61F 13/47236; A61F 13/47245; A61F 13/476; A61F 13/5605; A61F 13/5616
(Continued)

(56) References Cited

U.S. PATENT DOCUMENTS 4,500,316 A   2/1985 Damico
5,401,268 A   3/1995 Rodier
(Continued)

FOREIGN PATENT DOCUMENTS

| | | |
|---|---|---|
| EP | 1138294 A1 | 10/2001 |
| JP | 2010227241 A | 10/2010 |
| RU | 2277891 C2 | 6/2006 |

OTHER PUBLICATIONS

Russian Patent Office, Decision to Grant issued in RU application No. 2019139870/03(078379), dated Jun. 25, 2020 with English Translation (22 pages).
(Continued)

*Primary Examiner* — Catharine L Anderson
(74) *Attorney, Agent, or Firm* — Wood Herron & Evans LLP (57) ABSTRACT

An absorbent article having a main body having a liquid-permeable topsheet, a liquid-impermeable backsheet and an absorbent core sandwiched between the topsheet and the backsheet is disclosed. The main body has longitudinal and transversal axes. The article has two wings extending asymmetrically outward from a crotch portion of the main body with respect to the longitudinal axis. The wings each have a means for fastening them to a garment when folded over the main body towards the longitudinal axis. The fastening means for each wing are offset from each other in the longitudinal direction. A method for manufacturing the absorbent article is also disclosed.

23 Claims, 7 Drawing Sheets

(51) Int. Cl.
*A61F 13/15* (2006.01)
*A61F 13/472* (2006.01)

(52) U.S. Cl.
CPC ...... *A61F 13/15756* (2013.01); *A61F 13/476* (2013.01); *A61F 13/47245* (2013.01)

(58) Field of Classification Search
USPC .............................................. D24/124–126
See application file for complete search history.

(56) References Cited

U.S. PATENT DOCUMENTS

| 10,258,513 B2* | 4/2019 | Kuramochi ......... A61F 13/4704 |
| 2004/0138636 A1 | 7/2004 | Cardin et al. |
| 2005/0283131 A1 | 12/2005 | Zander et al. |

OTHER PUBLICATIONS

International Preliminary Report on Patentability for International Application No. PCT/EP2017/067068, dated Oct. 25, 2019, 18 pages.
International Preliminary Report on Patentability for International Application No. PCT/EP2017/067071, dated Oct. 25, 2019, 21 pages.
International Preliminary Report on Patentability for International Application No. PCT/EP2018/068232, dated Oct. 23, 2019, 21 pages.
International Preliminary Report on Patentability for International Application No. PCT/EP2018/068233, dated Oct. 21, 2019, 16 pages.
International Search Report and Written Opinion for International Application No. PCT/EP2017/067068, dated Jan. 8, 2018, 15 pages.
International Search Report and Written Opinion for International Application No. PCT/EP2017/067071, dated Jan. 8, 2018, 20 pages.
International Search Report and Written Opinion for International Application No. PCT/EP2018/068232, dated Aug. 16, 2018, 17 pages.
International Search Report and Written Opinion for International Application No. PCT/EP2018/068233, dated Aug. 17, 2018, 17 pages.
Japanese Patent Office, Office Action issued in JP application No. 2020-500068, dated Feb. 2, 2021 with partial English Translation (14 pages).

* cited by examiner

ABSORBENT ARTICLE AND METHOD FOR MANUFACTURING AN ABSORBENT ARTICLE

CROSS REFERENCE TO RELATED APPLICATIONS

This is a U.S. National Phase application of PCT/EP2018/068233, filed Jul. 5, 2018, which claims priority to PCT/EP2017/067068, filed Jul. 7, 2017 and PCT/EP2017/067071, filed Jul. 7, 2017, the disclosures of all of which are incorporated herein by reference in their entireties for all purposes.

TECHNICAL FIELD

The present disclosure relates to an absorbent article comprising a main body having a liquid-permeable topsheet, a liquid-impermeable backsheet and an absorbent core sandwiched between said topsheet and said backsheet, said main body being arranged along a longitudinal axis and a transversal axis extending in a perpendicular direction in relation to the longitudinal axis, said main body defining a front portion, a back portion and a crotch portion; wherein said article comprises a first wing and a second wing extending outwardly from said crotch portion of the main body in opposite directions in an asymmetric manner with reference to the longitudinal axis, and generally along said transversal axis, said wings being provided with fastening means configured for fastening said wings to a garment when being folded over said main body and towards said longitudinal axis.

The present disclosure also relates to a method for manufacturing an absorbent article having a longitudinal extension along a longitudinal axis and a transverse extension along a transverse axis, said article defining a front portion, a back portion and a crotch region. Furthermore, the method comprises the steps of: forming a main body by providing a liquid-permeable topsheet, providing a liquid-impermeable backsheet and sandwiching an absorbent body between said topsheet and said backsheet; forming a first wing and a second wing configured so as to extend outwardly from said main body in opposite directions and generally along said transversal axis; and providing said wings with fastening means for fastening said wings to a garment when being folded over said main body and towards said longitudinal axis.

BACKGROUND

Absorbent articles, for example in the form of sanitary napkins and panty liners, are well known. The general purpose of such absorbent articles is to absorb, distribute and store various types of body exudates while providing a high level of comfort and sense of dryness to the wearer during use of the absorbent article. Also, such absorbent articles are arranged to prevent the wearer from getting the clothes soiled by body exudates.

A conventional sanitary napkin is normally designed with a main body which comprises a liquid-permeable topsheet, a liquid-impermeable backsheet and an absorbent core which is sandwiched between the topsheet and the backsheet. The main body is arranged along a longitudinal axis and a transversal axis which extends in a perpendicular direction in relation to the longitudinal axis.

Furthermore, absorbent articles in the form of sanitary napkins are often provided with two wings, i.e. two wing-shaped fastening elements, extending outwardly from the main body in opposite directions and generally along the transversal axis. The purpose of the wings is to allow fastening of the sanitary napkin to an undergarment of a user. To this end, the wings are arranged to be folded over the main body and towards said longitudinal axis. In order to allow fastening of the sanitary napkin to the undergarment, each wing is provided with fastening means such as an adhesive material. In this manner, the sanitary napkin can be attached and held in place in the undergarment during use.

According to prior art, the wings of a sanitary napkin can be formed in a symmetrical manner, i.e. so that the entire sanitary napkin can be said to define a contour which is symmetrical with reference to its longitudinal axis. Alternatively, it is also known that the wings can be formed in an asymmetrical manner with reference to the longitudinal axis.

A previously known absorbent article having asymmetrical wings of the above-mentioned type is known from the patent document U.S. Pat. No. 5,401,268. This document shows a sanitary napkin having two wings which are arranged asymmetrically along opposite sides of a longitudinal edge of the napkin.

The wings disclosed in U.S. Pat. No. 5,401,268 are formed of two triangular pieces which comprise semi-circular indentations on the base of said pieces, and also a rounded cutout at the top of each triangular piece. The purpose of the wings shown in U.S. Pat. No. 5,401,268 is to provide a relatively large surface for fixing the sanitary napkin to an undergarment.

Even though the article disclosed in U.S. Pat. No. 5,401,268 fulfills the basic requirements regarding absorbent articles provided with wing-shaped fastening elements, there is a need for further improvements within this field of technology.

In particular, there is an increasing requirement to provide a more optimized use of a fastening means, comprising an adhesive, on each wing. In this regard, manufacturers of absorbent articles are often limited to using strips of adhesive material applied on each wing.

In such a process, there is a need to use a sufficient amount of adhesive, while at the same time minimizing the use of release paper, which is regarded as causing a relatively high cost.

Furthermore, it can be noted that the wings of the article shown in U.S. Pat. No. 5,401,268 are relatively long. This factor is of importance during manufacturing of said article, which is based on a process in which a rectangle of material—having dimensions exceeding the outer dimensions of the backsheet and topsheet of the article—is cut so as to correspond to the outer shape of the article. This means that a relatively high amount of material is needed since the entire article must fit within said rectangle. This also means that the longer the wings, the larger rectangle is needed. Consequently, a higher amount of material must be cut away and discarded during the manufacturing process, which is a disadvantage.

In summary, there is a need for improved articles having asymmetric wings with sufficient area and sufficient amount of adhesive but without resulting in too much waste material for forming the topsheet and backsheet.

Furthermore, the adhesive material must be used on the wings in a manner so that it does not give rise to any unwanted forces in the garment of the user, which otherwise may cause discomfort.

Consequently, there is a need for further improvements within the above-mentioned field of technology.

SUMMARY

In accordance with the present disclosure, there is provided an absorbent article with the purpose of solving the above-mentioned problems related to prior art within this field. In particular, the article is configured so as to provide a secure and stable attachment of a sanitary napkin to an undergarment, in order to provide a high level of comfort for the wearer while also providing the required absorbent properties. Also, the present disclosure aims at contributing to a cost-effective manufacturing process for sanitary napkins. In particular, it is a further object of the present disclosure to fulfill the need for relevant adhesive means but without causing an unnecessary waste of high amounts of material during a manufacturing process.

In accordance with the present disclosure, this object is obtained by means of an absorbent article comprising a main body having a liquid-permeable topsheet, a liquid-impermeable backsheet and an absorbent core sandwiched between said topsheet and said backsheet, said main body being arranged along a longitudinal axis and a transversal axis extending in a perpendicular direction in relation to the longitudinal axis, said main body defining a front portion, a back portion and a crotch portion; wherein said article comprises a first wing and a second wing extending outwardly from said crotch portion of the main body in opposite directions in an asymmetric manner with reference to the longitudinal axis, and generally along said transversal axis, said wings being provided with fastening means configured for fastening said wings to a garment when being folded over said main body and towards said longitudinal axis. Furthermore, the first wing comprises a first fastening means and the second wing comprises a second fastening means, said first and second fastening means are offset from each other in the longitudinal direction of the article.

The first and second fastening means being positioned transversally on each wing in a manner so that said first and second fastening means are not aligned along a common longitudinal direction. The first and second fastening means are displaced from each other in the longitudinal direction of the article.

The present disclosure fulfills the requirements on sanitary napkins to be securely fitted and held in place in an undergarment of a wearer. With particular reference to the fastening means on each wing, the disclosure provides an advantage since it contributes to reducing the waste of material for the backsheet and topsheet during a manufacturing process.

The first fastening means and the second fastening means may be positioned at least partly on opposite sides of the transversal axis X1. The first fastening means and the second fastening means may also be positioned entirely on opposite sides of the transversal axis X1.

The first fastening means and the second fastening means are positioned on opposite sides of the longitudinal axis Y1. Each one of said fastening means is also offset from each other in the transversal direction of the article.

The absorbent article may be configured so that each of the fastening means comprises a fastening material and forms a first and second fastening area. The fastening material may be adhesive- or mechanical.

The absorbent article may be configured so that the first and second fastening area defines a centre point, wherein the centre point on the first fastening area is offset from the centre point on the second fastening area in the longitudinal direction of the article.

The absorbent article may be configured so that said wings extend generally along a common straight line which defines a first angle with respect to said transversal axis which exceeds 0° but which is less than 45°. The first wing may be formed with an outer edge which includes a first point in the form of a transversally outermost point, and the second wing is formed with an outer edge which includes a second point in the form of a transversally outermost point, and wherein said straight line extends through the first point and the second point. The first angle may be within the interval 10°-35°.

The absorbent article may be configured so that the position of the first fastening area does not coincide with the position of the second fastening area as mirrored along the machine direction of the article.

The absorbent article may be configured so that each wing is formed with an outer edge which defines at least one arc of a circle coinciding with a section of the outer edge and having a defined radius, said section extending between a first point and a second point along said outer edge where said arc no longer coincides with said outer edge, and wherein said radius is within the interval of 40-500 mm. An advantage with this configuration is that there will be a reduced risk that a user folds a wing over the other wing during use, i.e. so that the adhesive on the first wing is positioned on top of the second wing (instead of being placed on the user's undergarment), which is a disadvantage. The fact that the wings are formed with the above-mentioned arc-shaped outer edge will minimize this risk.

Furthermore, the absorbent article may be configured so that each wing has an outer edge which is generally straight and parallel to the longitudinal axis.

According to one embodiment is the fastening means on each wing configured closer to the outer edge of the wing than to the main body of the article.

Each fastening means may be constituted by one or more one or more discrete fastening areas, extending in the longitudinal direction of the article or in the transversal direction of the article. Each fastening means may for example be constituted by one of more generally rectangular strips. A generally rectangular shape is intended to encompass also that, for instance, the corners of the strips may be rounded, or that the edges of the strips may not be completely linear.

Each fastening means may be constituted by two or more discrete fastening areas, for example generally rectangular strips extending in the longitudinal direction of the article, wherein at least one of the discrete fastening areas on each of the fastening means may be positioned at least partly on opposite sides of the transversal axis X1.

Furthermore, at least one of the discrete fastening areas on each of said fastening means may be positioned entirely on opposite sides of the transversal axis X1.

Furthermore, at least one of the discrete fastening areas on each of the fastening means may be positioned entirely on opposite sides of the transversal axis X1 and at least one of the discrete fastening areas on each of the fastening means may be positioned at least partly on opposite sides of the transversal axis X1.

Also, all discrete fastening areas on each of the fastening means may be positioned entirely on opposite sides of the transversal axis X1.

The fastening means may be adhesive- and/or mechanical fastening means.

Furthermore, each wing is formed with an outer edge and at least the part of each fastening means positioned closest to the outer edge on each of the wings may be positioned entirely on opposite sides of the transversal axis X1. If the fastening means is constituted by two or more generally rectangular strips extending in the longitudinal direction of the article, the strip positioned closest to the outer edge on each of the wings may be positioned partly, or entirely on opposite sides of the transversal axis X1.

Also, said radius may be within the interval of 50-400 mm.

Furthermore, said radius may be within the interval of 50-300 mm.

Said fastening means may be covered, during manufacturing, by a release layer.

The absorbent article may be configured so that each wing defines a first straight line between the first point and a further point, and a second straight line along an upper edge section, wherein the first line defines a second angle ($\alpha 2$) with respect to the longitudinal axis and wherein the second line defines a third angle ($\alpha 3$) with respect to the longitudinal axis, the magnitude of each angle ($\alpha 2$, $\alpha 3$) being chosen so that $\alpha 2 < \alpha 3$, or $\alpha 2 > \alpha 3$, or $\alpha 2 = \alpha 3$.

The magnitude of said second angle ($\alpha 2$) may be chosen so that: $10° < \alpha 2 < 65°$.

Also, the magnitude of said third angle ($\alpha 3$) may be chosen so that: $60° < \alpha 3 < 120°$.

Each wing may be formed with an area between said fastening means and the upper edge section which constitutes a grip tab.

Furthermore, the absorbent article may be configured so that a first distance, as defined between the outer edge of each wing and the longitudinal axis, is in the range of 40-100 mm.

Furthermore, a second wing folding edge may be defined where each wing can be folded during use of the article, said second wing folding edge having a length which is within the interval 10-80% of the full length of the main body, and preferably 25-65% of the full length of the main body.

The absorbent article may be configured so that each longitudinal side of the absorbent core at least partly defines a core edge which is generally parallel to the longitudinal axis.

The absorbent article may be configured so that each absorbent core generally follows the outer edge of the main body and defines an edge region of the main body which is generally equally wide along the entire periphery of the absorbent core.

The absorbent article may be configured so that said wings are formed with an area between said fastening means and a further edge which constitutes a grip tab.

The absorbent article may also be constituted with a second wing folding edge which extends between the transversally innermost points in the longitudinal direction of the main body in the crotch area. The second wing folding edge coincides with the wing extension in the longitudinal direction from the main body. The extension of the first fastening means along the first wing, in the longitudinal direction of the article, may be at least ¼ of the total length of the second wing folding edge, or at least ½ of the total length of the second wing folding edge, or at least % of the total length of the second wing folding edge. The extension in the longitudinal direction of the second fastening means along the second wing folding edge may also be at least ¼ of the total length of the second wing folding edge, or at least ½ of the total length of the second wing folding edge.

The absorbent article may also comprise a further fastening means positioned along the main body on a garment-facing side of said backsheet.

There is also provided a method for manufacturing an absorbent article having a longitudinal extension along a longitudinal axis and a transverse extension along a transverse axis, said article defining a front portion, a back portion and a crotch region, said method comprising forming a main body by providing a liquid-permeable topsheet, providing a liquid-impermeable backsheet and sandwiching an absorbent body between said topsheet and said backsheet; forming a first wing and a second wing configured so as to extend outwardly from said main body in opposite directions in an asymmetric manner with reference to the longitudinal axis and generally along said transversal axis; and providing said wings with fastening means for fastening said wings to a garment when being folded over said main body and towards said longitudinal axis. Furthermore, the method comprises the following steps: arranging said first wing so as to support a first fastening means; arranging said second wing so as to support a second fastening means; positioning said first and second fastening means transversally on each wing in a manner so that said first and second fastening means are not aligned along a common longitudinal direction.

Further advantages and advantageous features of the present disclosure are disclosed in the following description and in the dependent claims.

BRIEF DESCRIPTION OF THE DRAWINGS

The present disclosure will be described in greater detail below with reference to the FIGS. shown in the appended drawings.

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1:
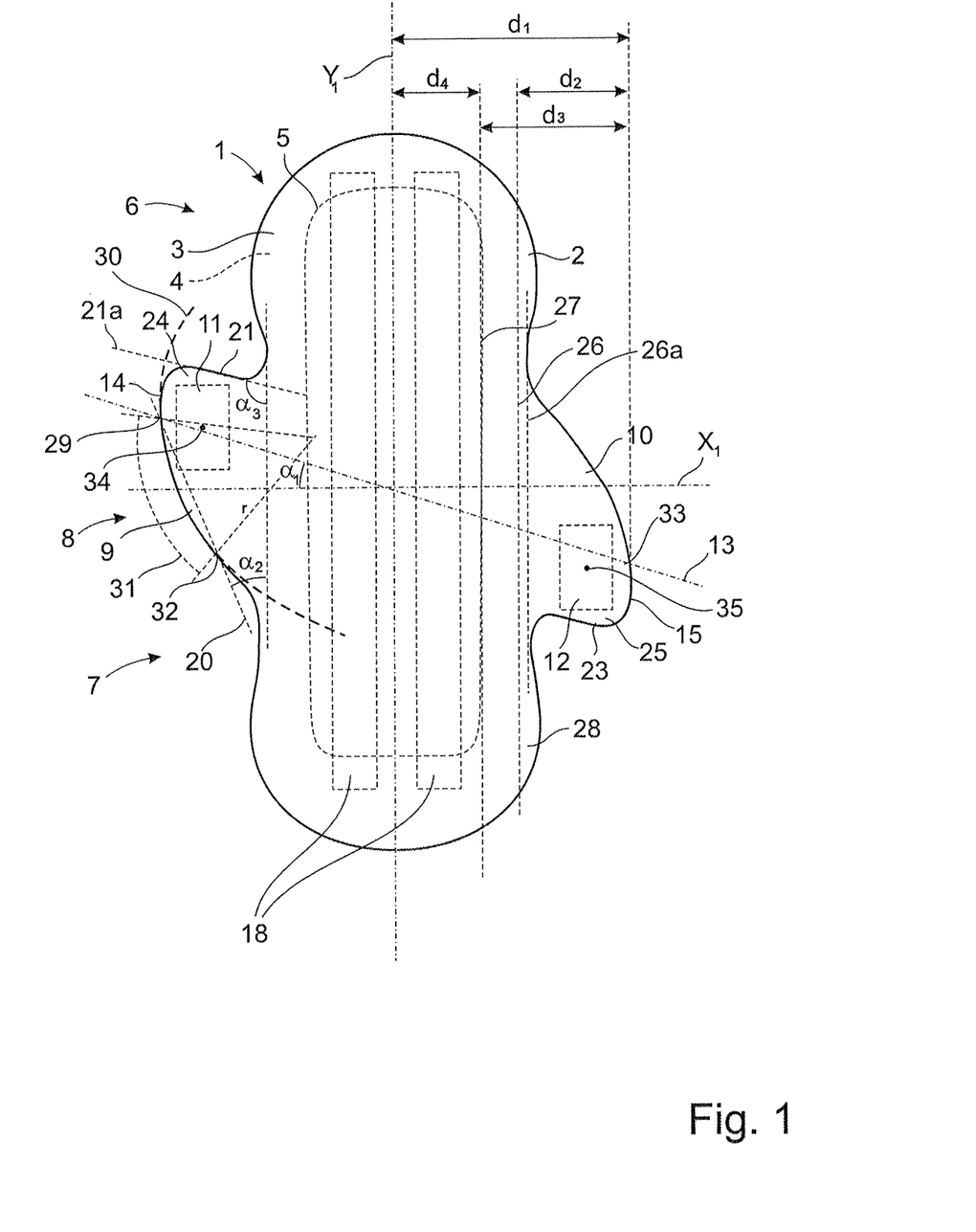
FIG. 1 shows a view from above of an absorbent article in the form of a sanitary napkin according to an embodiment of the present disclosure.

With initial reference to FIG. 1, there is shown a view from above of an absorbent article in the form of a sanitary napkin 1 manufactured in accordance with an embodiment of the present disclosure. The sanitary napkin 1 is based on an absorbent structure for absorbing body exudates from a wearer in order to provide a dry, comfortable and odor-free feeling for the wearer.

From FIG. 1 it can be understood that the sanitary napkin 1 comprises a main body 2 with a liquid-permeable topsheet 3 and a liquid-impermeable backsheet 4. The sanitary napkin 1 also comprises an absorbent core 5 which is sandwiched between the topsheet 3 and the backsheet 4. The topsheet 3 is arranged at the surface of the sanitary napkin 1, i.e. the side facing the wearer. The backsheet 4 is arranged at the underside of the sanitary napkin 1, i.e. the side facing an undergarment (not shown) of the wearer. Furthermore, both the topsheet 3 and the backsheet 4 extend laterally outside of the absorbent core 5 along the whole perimeter of the main body 2.

The absorbent core shown in FIG. 1 has a substantially rectangular design. However, the invention is not limited to this particular design.

According to further embodiments, one or more additional layers may be provided in the absorbent article 1. For example, an acquisition layer may be arranged between the absorbent core 4 and the topsheet 3. Such an additional layer can for example be in the form of an airlaid layer, a spunlace layer, a high-loft, foam or any other type of material layer which may be used in an absorbent article in order to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven can be produced with fluff, wood pulp, and here the fluff fibres are dispersed into a fast moving air stream and condensed onto a moving screen by means of pressure and vacuum. The web can be bonded with resin and/or thermal plastic resin dispersed with the pulp. The web can be thermobonded (by heat), latex bonded (by adhesive) or multibonded (a combination of thermo and latex bonding) or mechanically bonded (high compression and temperature, bonding by hydrogen). The grammage of the airlaid nonwoven may be for example from 50 to 100 gsm.

The topsheet 3, backsheet 4 and the absorbent core 5 may consist of or comprise any materials suitable for their particular purposes, as will be discussed in further detail below. Also, the above-mentioned layers 3, 4, 5 may be connected to each other by any conventional means such as by means of an adhesive, heat bonding or ultrasonic bonding.

Furthermore, and although not shown in the drawings, the sanitary napkin 1 can be configured in a manner having different material layers, densities or material components as seen along a horizontal plane of the sanitary napkin 1, i.e. in addition to being configured with different layers in the vertical direction.

As shown in FIG. 1, the sanitary napkin 1 has a longitudinal extension along a longitudinal axis Y1 and a transverse extension along a transverse axis X1. Furthermore, the sanitary napkin 1 can be said to be divided into a front portion 6, a back portion 7 and a crotch portion 8. The front portion 6 is intended to be oriented in a direction towards the wearer's belly during use of the sanitary napkin 1.

Furthermore, according to the embodiment, the sanitary napkin 1 is formed with two fastening wings 9, 10, or fastening tabs, which are configured for fastening the napkin 1 to an undergarment of the wearer. More precisely, the sanitary napkin 1 comprises a first wing 9 and a second wing 10, each of which extends outwardly from the main body 2 and in opposite directions. The wings 9, 10 extend generally along the direction of the transversal axis X1. Also, the wings 9, 10 are provided with fastening means 11, 12, which according to the embodiment are in the form of one or more adhesive areas which are configured for fastening the wings 9, 10 to the user's undergarment when the wings 9, 10 are folded under the main body 2 in a direction towards the longitudinal axis Y1. The first wing 9 comprises a first fastening means 11 and the second wing 10 comprises a second fastening means 12, said first and second fastening means 11, 12 are offset from each other in the longitudinal direction of the article.

Furthermore, each adhesive area of the fastening means 11, 12 can be said to define a centre point 34, 35, corresponding to a centre of mass for said adhesive area. According to known technology, such a centre point can be defined for any area, irrespective of its shape.

Each wing 9, 10 has an outer edge 14, 15 which according to an embodiment shown in FIG. 1 is curve-shaped, i.e. it defines an outwardly extending curve along the direction of the absorbent article 1. In particular, the outer edge 14 of the first wing 9 defines a first point 29 which is an outermost point in the sense that it defines a point along the outer edge 14 which has the greatest distance to the longitudinal axis Y1 of all the points along the outer edge 14. The curve-shaped outer edge 14 is formed in a manner so as to provide certain advantages, as mentioned above.

In order to obtain these advantages, the outer edge 14 defines in particular at least one arc of a circle which coincides with a section 31 of the outer edge 14 and has a defined radius r. The section 31 extends between the first point 29 and a second point 32 along the outer edge 14 where the arc 30 no longer coincides with said outer edge 14.

In the embodiment shown in FIG. 1, the first point 29 is constituted by the transversally outermost point 29 of the outer edge 14. The invention is however not limited to this embodiment only, as will be described in greater detail below. With reference to FIG. 1, the section 31 of the outer edge 14 extends from the outermost point 29 and to the second point 32 where the arc 30 does not coincide with the outer edge 14.

In a corresponding manner, the second wing 10 is shaped in the same manner as the first wing 9 and has a second outer edge 15 with a second point 33 which is an outermost point in the same sense as the first point 29, i.e. it defines a point which has the greatest distance to the longitudinal axis Y1 of all the points along the second outer edge 15.

Furthermore, a first wing folding edge 26 is defined as a part of the longitudinal side of the main body 2 where each wing 9, 10 meets the main body 2 and along which each wing 9, 10 can be folded when the sanitary napkin 1 has been manufactured. The first wing folding edge 26 as shown in FIG. 1 is defined as a line which is parallel to the longitudinal axis Y1.

Consequently, the first wing folding edge 26 is defined as part of the longitudinal side of the main body 2 where each wing 9, 10 meets the main body 2 and along which each wing 9, 10 is folded when the absorbent article 1 is manufactured.

As mentioned, the first wing folding edge 26 defines a line along which the corresponding wing 10 can be folded during manufacturing of the sanitary napkin 1. During use of the sanitary napkin 1, however, the wings 9, 10 are normally folded along a line which is adapted to the size of the undergarment. Consequently, as also shown in FIG. 1, a second wing folding edge 26a is defined as a line along which each wing 9, 10 can be expected to be folded during use of the sanitary napkin 1. The second wing folding edge 26a extends between the transversally innermost points in the longitudinal direction of the main body in the crotch area. The second wing folding edge 26a coincides with the wing extension in the longitudinal direction from the main body. The extension of the first fastening means along the first wing, in the longitudinal direction of the article, may be at least ¼ of the total length of the second wing folding edge, or at least ½ of the total length of the second wing folding edge. The extension in the longitudinal direction of the second fastening means along the second wing folding edge may also be at least ¼ of the total length of the second wing folding edge, or at least ½ of the total length of the second wing folding edge.

According to embodiments, the second wing folding edge 26a is configured so that the length along which it is folded is within the interval 10-80% of the full length of the main body, and preferably 25-65% of the full length of the main body, depending on the size and the desired properties of the sanitary napkin 1.

Figure 1A:
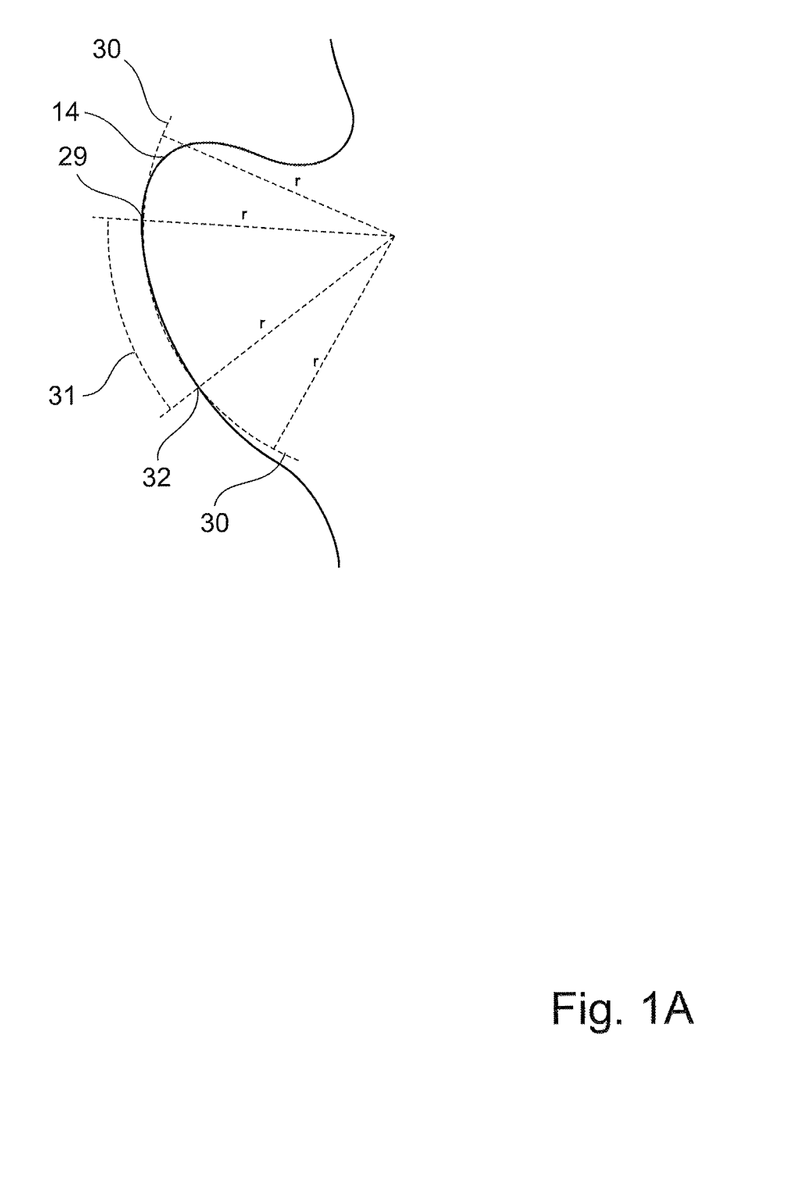
FIG. 1A shows an enlarged portion of the article according to FIG. 1.

FIG. 1A is an enlarged view showing a portion of the article 1 including the arc 30 of a circle and the section 31. As shown in the embodiment of FIG. 1A, the outer edge 14 is formed in a manner so that it defines an arc 30 of a circle which extends along the outer edge 14 and partly coincides with a section 31 of said outer edge 14. The arc 30 has a defined radius r, which may be within the interval 40-500 mm. Furthermore, the section 31 extends between the first point 29 and the second point 32, wherein said second point 32 is a point along the outer edge 14 where the arc 30 no longer coincides with the outer edge 14.

As indicated in FIG. 1, the two wings 9, 10 are arranged in an asymmetric manner so that they extend generally along a common straight line 13 which defines a first angle α1 with respect to the transversal axis X1. According to an embodiment, the magnitude of the first angle α1 exceeds 0° but is less than 45°. According to an embodiment, the first angle α1 may be within the interval 10-35°. It should be noted that the wings 9, 10 can be arranged so that they are displaced in relation to each other in the longitudinal direction of the sanitary napkin 1.

In order to clearly define the extension of the above-mentioned straight line 13 shown in FIG. 1, it can be noted that said straight line 13 extends through the above-mentioned first point 29 and the second point 33, which correspond to the transversally outermost points along the outer edges 14, 15.

Figure 2:
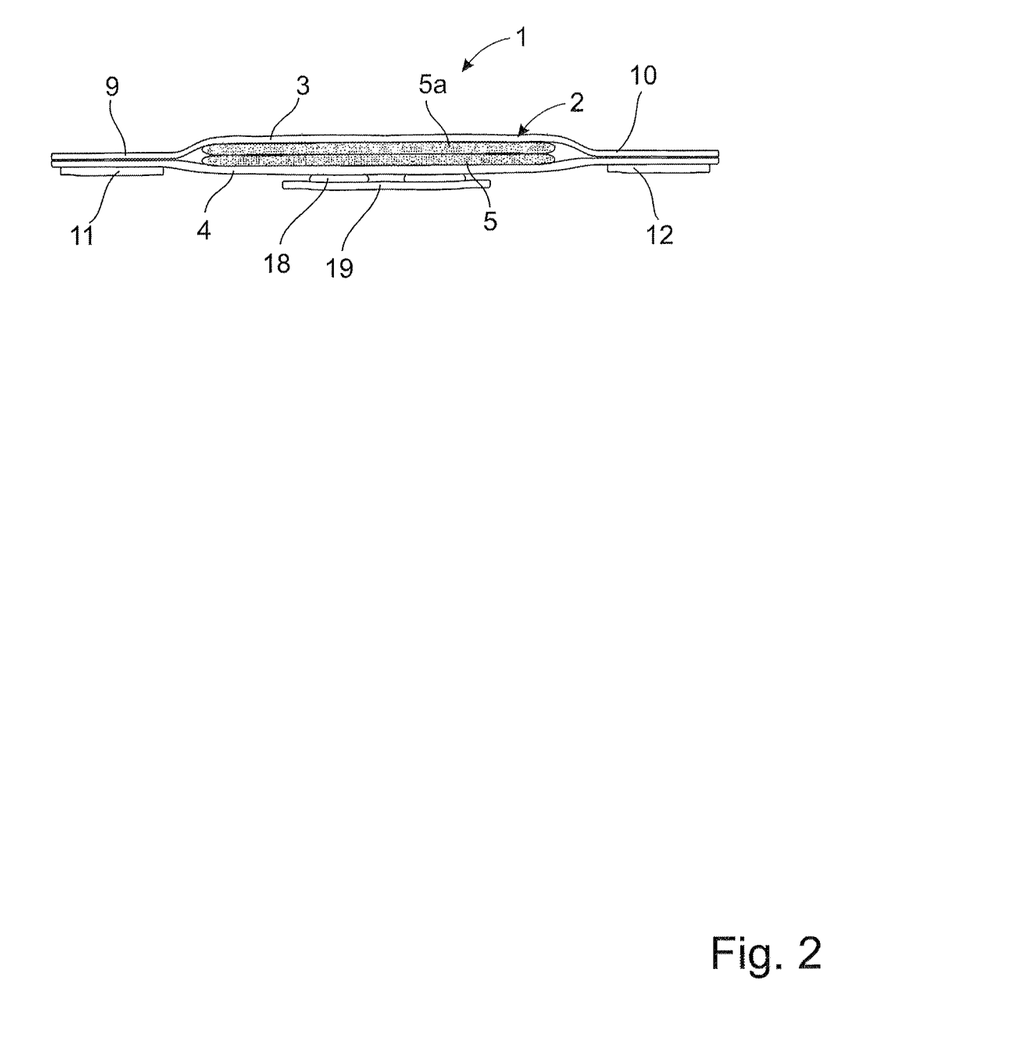
FIG. 2 shows a cross-sectional view of the sanitary napkin.

FIG. 2 is a cross-sectional view as seen along the straight line 13 shown in FIG. 1. The absorbent core 5 is sandwiched between the topsheet 3 and the backsheet 4. As mentioned above, an acquisition layer 5a, suitably of airlaid material, can be arranged between the absorbent core 5 and the topsheet 3. Also, the two wings 9, 10 are formed so as to extend in opposite directions from the main body 2. According to the embodiment, each of the wings 9, is provided with fastening means in the form of at least one adhesive area 11, 12, which is applied on the underside of each wing 9, 10, i.e. on the side which does not face the wearer. Furthermore, the main body 2 is also provided with further fastening means 18 for the purpose of fastening the sanitary napkin 1 onto an inner surface of an undergarment. Such further fastening means 18 may be in the form of one or several adhesive sections 18 which are arranged on the rear side of the backsheet 4 and which are arranged to extend along the longitudinal direction of the sanitary napkin 1.

As shown in FIG. 2, the adhesive sections 18 are covered with a release paper layer 19 when the sanitary napkin 1 is in its non-used condition. When the sanitary napkin 1 is to be used, the release paper layer 19 is removed by the user so that the sanitary napkin 1 can be fastened to the undergarment.

According to alternative embodiments, the sanitary napkin 1 can be provided with various types of fastening means in the form of frictional fasteners, mechanical fasteners such as a hook-and-loop fastener, or combinations of different types of fasteners, as previously known.

The properties and design of the various layers 3, 4, 5 which form part of the sanitary napkin 1 will now be described more in detail, with reference primarily to FIGS. 1 and 2.

According to an embodiment, the topsheet 3 is formed by a fluid permeable nonwoven fabric or film which is made of thermoplastic synthetic fibers. The topsheet 3 is sufficiently liquid-permeable to allow discharged body fluids to penetrate through the thickness of the topsheet 3. Also, the topsheet 3 is suitably manufactured from a material which is compliant and soft-feeling to the skin of the wearer.

According to different embodiments, the topsheet 3 may be manufactured from various web materials such as for example nonwoven films, foams, or combinations of the above-mentioned materials. The topsheet 3 may also be perforated.

Furthermore, the backsheet 4 is constituted by a liquid-impermeable and breathable layer such as a polymeric film, for example a film of polyethylene or polypropylene. According to different embodiments, the materials which can be used for the backsheet 4 include thin and flexible fluid impermeable plastic films, or fluid impermeable nonwoven materials, fluid impermeable foams and fluid impermeable laminates.

According to the embodiment shown in the drawings, the backsheet 4 is formed by a single layer, but can alternatively be formed by a multi-layered structure, i.e. a laminate, wherein at least one layer is fluid impermeable. Furthermore, the backsheet 4 can optionally be elastic in any direction. Also, backsheet materials which are not fully liquid impermeable but only resistant to fluid penetration may be used, particularly in cases where relatively small amounts of body exudates are expected to be absorbed by the sanitary napkin 1.

According to further embodiments, the backsheet 4 may be breathable, implying that air and vapor may pass through the backsheet 4. Furthermore, the backsheet 4 may optionally have an outer, garment-facing surface of a textile material such as nonwoven.

Furthermore, the wings 9, 10 are formed in a manner in which the topsheet 3 and the backsheet 4 are laminated and formed with the wings 9, 10 being integrated as shown in the drawings. This means that the outer edges 14, 15 are cut in the desired form during a manufacturing process for the sanitary napkin 1. According to an alternative embodiment, which is not shown in the drawings, the wings can be manufactured separately and then supplied and finally attached to the main body during a final manufacturing process.

Furthermore, according to the embodiment shown in FIGS. 1, 1A and 2, the sanitary napkin 1 comprises an absorbent core 5 which is formed by one or more layers comprising fibres of cellulosic fluff pulp. According to alternative embodiments, the absorbent core 5 can be made up of any suitable absorbent or fluid-absorbing material as known in the art, for example foam, fiber waddings and similar materials. As mentioned above, different types of material layers can be used, alone or in combination, for example airlaid, spunlace and highloft material, depending on the required properties and the field of use of the sanitary napkin 1 in question.

According to one embodiment, the absorbent article is a liner, in which case the absorbent core may only be made of one thin material, for example a nonwoven layer.

According to a further embodiment, the absorbent core 5 comprises superabsorbent material. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight. According to an embodiment, the amount of said superabsorbent particles is at least 10% by weight, i.e. in relation to the total weight of the absorbent core 5.

The superabsorbents are mixed into the material of the absorbent core 5. The absorbent core may further incorporate components for improving the properties of the absorbent core 5. Some examples of such components are binder fibers, fluid-dispersing materials, fluid acquisition materials, etc. as known in the art. According to an embodiment, a mixture of cellulose fluff pulp and superabsorbent articles is mixed in a generally homogeneous manner throughout the entire absorbent core 5.

According to further embodiments, the absorbent core 5 may be a homogeneous structure or may be a layered structure with laminates of the same or different materials. The absorbent layers may have uniform thickness or may vary in thickness in different parts of the layers. Also, the basis weight and composition of the absorbent core 1 may vary within such absorbent layers.

Furthermore, as known by the skilled person, the various layers of the sanitary napkin 1 can suitably be attached by means of layers of adhesive material. Such adhesive layers are not shown in the drawings.

With reference to FIG. 1, the wing 9 is formed so that a further straight line 20 is defined as extending through the first point 29 and the second point 32. Also, another straight line 21*a* is formed along an upper edge section 21 of the wing 9. More precisely, the first-mentioned line defines a second angle $\alpha 2$ with respect to the longitudinal axis Y1 and the second line 21*a* defines a third angle $\alpha 3$ with respect to the longitudinal axis Y1. In the embodiment shown in FIG. 1, the magnitude of each angle $\alpha 2$, $\alpha 3$ is chosen so that $\alpha 2 < \alpha 3$. However, the invention is not limited to such selection of angles only, but can alternatively be arranged in a manner in which $\alpha 2 > \alpha 3$, or even $\alpha 2 = \alpha 3$.

The second wing 10 is arranged in a similar manner as the first wing 9 but is reversed (i.e. "upside-down") as compared with the first wing 9, i.e. with lines corresponding to the above-mentioned lines 20, 21*a*.

According to the shown embodiment, the wings 9, 10 are arranged in a generally parallel manner, while being connected to the main body 2 in a slightly displaced manner.

Consequently, the wings 9, 10 form an asymmetric design due to the design of the wings 9, and also due to the fact that they extend generally along the above-mentioned common straight line 13 which defines a first angle $\alpha 1$ with respect to the transversal axis X1.

According to the embodiment shown in FIG. 1, the third angle $\alpha 3$ is greater than 90°, which means that a relatively small area 24 is formed between the adhesive area 11 and the upper edge section 21, which area 24 is not covered with any adhesive. This area 24 forms a grip tab which simplifies gripping and handling of the wings 9, 10 during fastening of the sanitary napkin 1 in an undergarment, and also during removal of the sanitary napkin 1 from the undergarment. It should be noted that a grip tab can be provided also in the case in which the third angle $\alpha 3$ is less than 90°. Such an embodiment will be described below with reference to FIG. 5.

In the following, certain dimensions and measurements relating to an embodiment of the present disclosure will now be described with reference to FIG. 1. As indicated, a first distance d1, as defined between the outermost point 29, 33 of each wing (here shown only with reference to the second wing 10) and the longitudinal axis Y1 is in the range of 40-100 mm, preferably 50-90 mm, most preferably 60-90 mm. According to a particular embodiment, the first distance d1 is approximately 77 mm. This corresponds to the distance from the centre of the absorption body 4 to the outermost points 29, 33 of each wing 9, 10.

Furthermore, a first wing folding edge 26 is defined as a part of the longitudinal side of the main body 2 where each wing 9, 10 meets the main body 2 and along which each wing 9, 10 can be folded when the sanitary napkin 1 has been manufactured. The first wing folding edge 26 as shown in FIG. 1 is defined as a line which is parallel to the longitudinal axis Y1.

Consequently, the first wing folding edge 26 is defined as part of the longitudinal side of the main body 2 where each wing 9, 10 meets the main body 2 and along which each wing 9, 10 is folded when the absorbent article 1 is manufactured.

As mentioned, the first wing folding edge 26 defines a line along which the corresponding wing 10 can be folded during manufacturing of the sanitary napkin 1. During use of the sanitary napkin 1, however, the wings 9, 10 are normally folded along a line which is adapted to the size of the undergarment. Consequently, as also shown in FIG. 1, a second wing folding edge 26*a* is defined as a line along which each wing 9, 10 can be expected to be folded during use of the sanitary napkin 1. According to embodiments, the second wing folding edge 26*a* is configured so that the length along which it is folded is within the interval 10-80% of the full length of the main body, and preferably 25-65% of the full length of the main body, depending on the size and the desired properties of the sanitary napkin 1.

A second distance d2 can be defined between the first wing folding edge 26 and the corresponding outermost point 30 of the corresponding wing 10, said second distance d2 being in the range of 20-60 mm, preferably 25-50 mm, most preferably 24-45 mm. According to a particular embodiment, the second distance d2 is approximately 39 mm. A further way of defining the magnitude of the second distance d2 is by defining it in relation to the full width of the sanitary napkin 1. According to embodiments, the ratio between the second distance d2 and the full width is in the range of 12-39%, preferably 16-32%, most preferably 16-29%.

Furthermore, a core edge 27 can be defined along at least a part of each longitudinal side of the absorbent core 5. As shown in FIG. 1, the core edge 27 is generally parallel to the longitudinal axis Y1. Also, a third distance d3, as defined between the core edge 27 and the outermost point 30 of the corresponding wing 10, is in the range of 29-69 mm, preferably 34-65 mm, most preferably 34-61 mm. According to a particular embodiment, the third distance d3 is approximately 49 mm. A further way of defining the magnitude of the third distance d3 is by defining it in relation to the full width of the sanitary napkin 1. According to embodiments, the ratio between the third distance d3 and the full width is in the range of 18-45%, preferably 21-42%, most preferably 21-40%.

Also, a fourth distance d4 is defined between the core edge 27 and the longitudinal axis Y1, said fourth distance d4 being in the range of 10-50 mm, preferably 15-45 mm, most preferably 20-40 mm. According to a particular embodiment, the fourth distance d4 is approximately 29 mm. A further way of defining the magnitude of the fourth distance d4 is by defining it in relation to the full width of the sanitary napkin 1. According to embodiments, the ratio between the fourth distance d4 and the full width is in the range of 6-33%, preferably 9-29%, most preferably 12-25%.

Also, the core edge 27 is according to the embodiment shown in the drawings generally parallel with the longitudinal axis Y1. In other embodiments, however, the core edge can be non-parallel in relation to the longitudinal axis Y1. In such cases, the above-mentioned distances d3 and d4 will be dependent on the position along the longitudinal axis Y1.

Furthermore, the absorbent core 5 is formed with a periphery which generally follows the outer edge of the main body 2 and defines an edge region 28 along the entire periphery of the main body 2.

Figure 3:
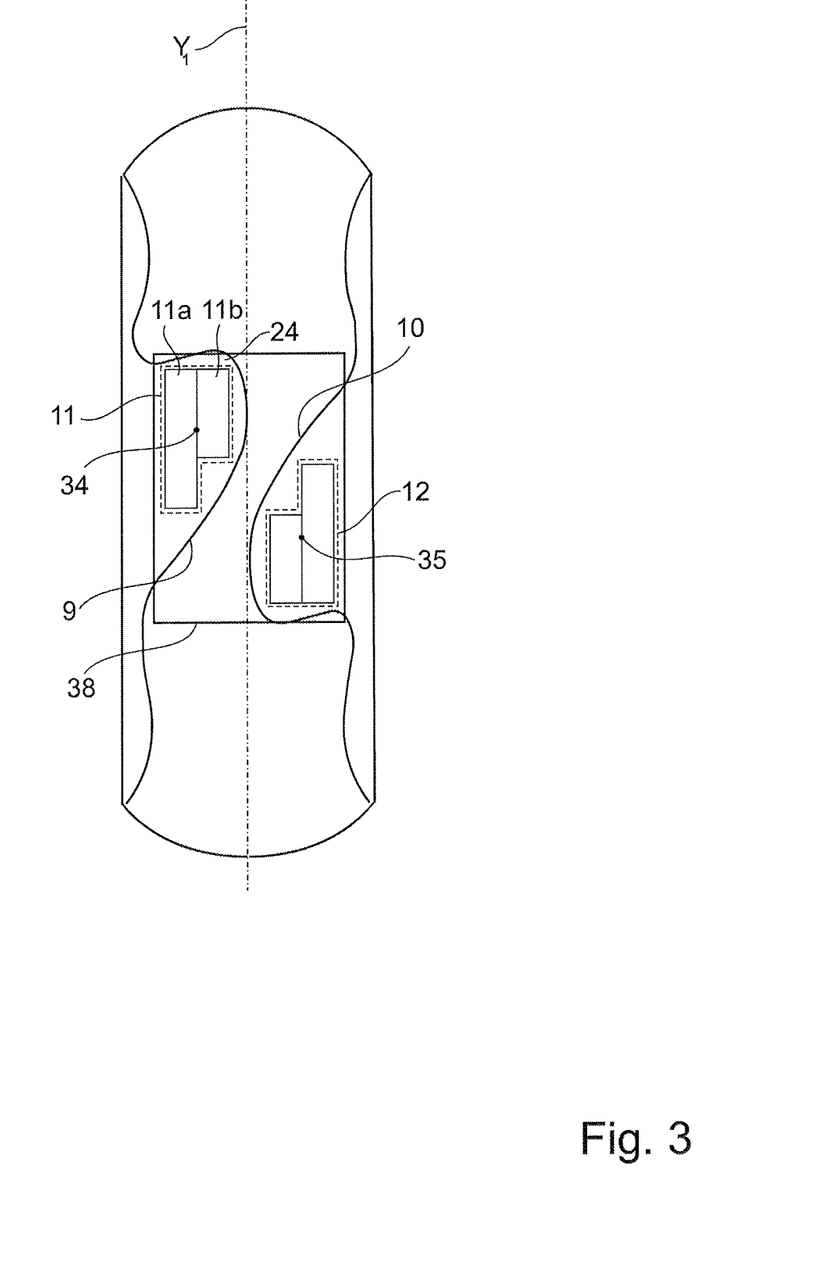
FIG. 3 shows a view from above of the sanitary napkin shown in FIGS. 1 and 2, in a condition as manufactured.

FIG. 3 shows the sanitary napkin according to FIGS. 1 and 2 but in a condition as manufactured, i.e. with the wings 9, 10 being folded. Not all components and features of the sanitary napkin 1 which are shown in FIGS. 1 and 2 are indicated with reference numerals in FIG. 3.

As indicated in FIG. 3, the main parts of the adhesive areas 11, 12 (schematically shown in FIG. 3 by means of broken lines) are located relatively close to the longitudinal axis Y1. Also, the adhesive areas 11, 12 are displaced in relation to each other along the longitudinal direction of the sanitary napkin 1. This contributes, during use of the sanitary napkin 1, to a secure and comfortable fit for the user, while maintaining adequate absorption properties.

According to the embodiment shown in FIG. 3, the first fastening means 11 forms an area which is composed of two longitudinally extending strips 11a, 11b of adhesive material. These strips 11a, 11b are arranged next to each other and extend from a point which is close to the grip tab 24. According to the embodiment, the strips 11a, 11b are of different length so as to fit the form of the wing 9. Furthermore, the combined area formed by the strips 11a, 11b can be said to define a centre point 34, as explained above.

Also, as shown in FIG. 3, the fastening means 11 of the first wing 9 and the fastening means 12 of the second wing 10 may be covered, during manufacturing of the article 1, by means of a release layer 38, and in certain embodiments, preferably in the form of a rectangular release paper.

The second fastening means 12 is arranged in a manner which corresponds to the first fastening means 11, i.e. it has a further centre point 35.

In summary, the first wing 9 supports a first fastening means 11 whereas the second wing 10 supports a second fastening means 12. The first and second fastening means 11, 12 are positioned transversally on each wing 9, 10 in a manner so that said first and second fastening means 11, 12 are not aligned along a common longitudinal direction configuration as manufactured and packaged. This configuration is also intended for the actual use of the article 1. In this manner, certain advantages are obtained. More precisely, the requirements on sanitary napkins to be securely fitted and held in place in an undergarment of a wearer while also contributing to reducing the waste of material for the backsheet and topsheet during a manufacturing process.

Furthermore, the fastening means 11, 12 are positioned on each wing 9, 10 in a manner so that the centre points 34, 35 are not positioned along a common longitudinal direction when the article 1 is in use and the wings 9, 10 are fastened to the user's undergarment. This means that the position of the first wing 9 does not coincide with the position of the second wing 10 as mirrored along the machine direction 26a of the article 1, i.e. along the second wing folding edge 26a shown in FIG. 1.

FIG. 3 shows an embodiment in which the outer edges 14, 15 of the wings 9, 10 are folded towards the longitudinal axis Y1. It should be noted that the outer edges can extend a further distance over the main body 2, i.e. so that they extend over the longitudinal axis Y1. It should be noted that, irrespective of the actual positions of the outer edges 14, 15, it is advantageous if the adhesive areas 11, 12 are positioned—when the wings 9, 10 are folded—in a manner so that they overlap and cooperate with the adhesive sections 18 on the rear side of the main body 2 during use.

Figure 4:
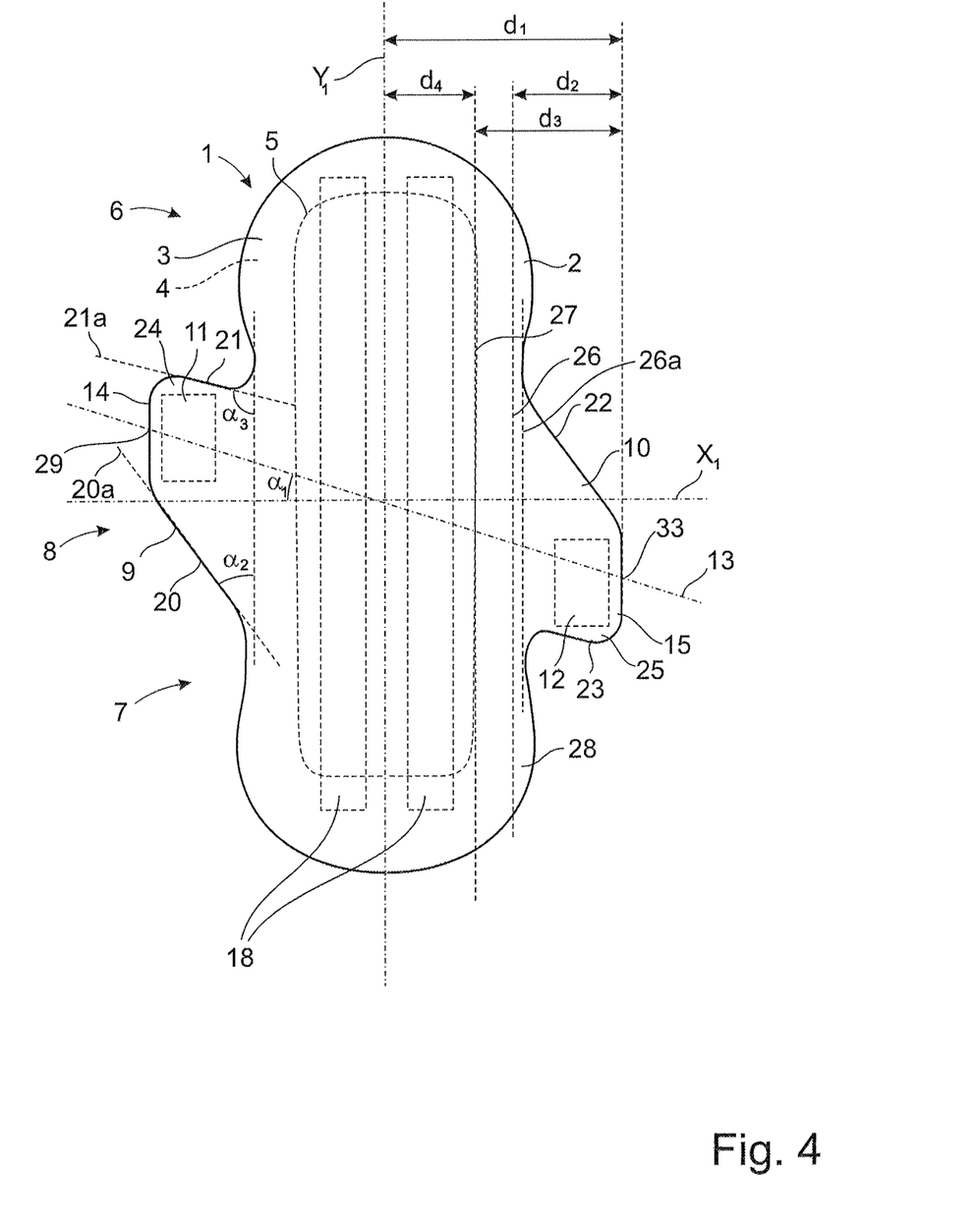
FIG. 4 shows a further embodiment of the present disclosure.

FIG. 4 shows a further embodiment of the present disclosure, in which each wing 9, 10 has an outer edge 14, 15 which is generally straight and parallel to the longitudinal axis Y1. This means that each one of the outer edges 14, 15 is cut off or otherwise shaped so as to form an outer, straight side edge which terminates each wing 9, 10 and which also is generally parallel to the longitudinal axis Y1.

The embodiment in FIG. 4 shows that the wings 9, 10 are arranged along a common straight line 13, in the same manner as the embodiment in FIG. 1. The points referred to as "transversally outermost points" 29, 33 (see also FIG. 1) are in the embodiment of FIG. 4 constituted by mid-points along each cut off outer edge 14, 15, i.e. points positioned halfway along each outer edge 14, 15 of each one of the wings 9, 10.

As mentioned, the fastening means 11, 12 which is arranged on each one of the wings 9, 10 is according to an embodiment in the form of an area which supports an adhesive material. These adhesive areas 11, 12 are generally rectangular and positioned on each wing 9, 10 in a manner so that they are displaced in relation to each other in the longitudinal direction of the article 1, and also so that they extend along generally the entire transversal length of each corresponding wing 9, 10.

The arrangement of the fastening means 11, 12 according to the present disclosure provides an advantage in that it increases the stability of each wing 9, 10. Also, the sanitary napkin 1 can be positioned and attached to an undergarment in a secure and comfortable manner, without any shearing forces acting on the undergarment, which otherwise could be detrimental to the comfort of the wearer.

Figure 5:
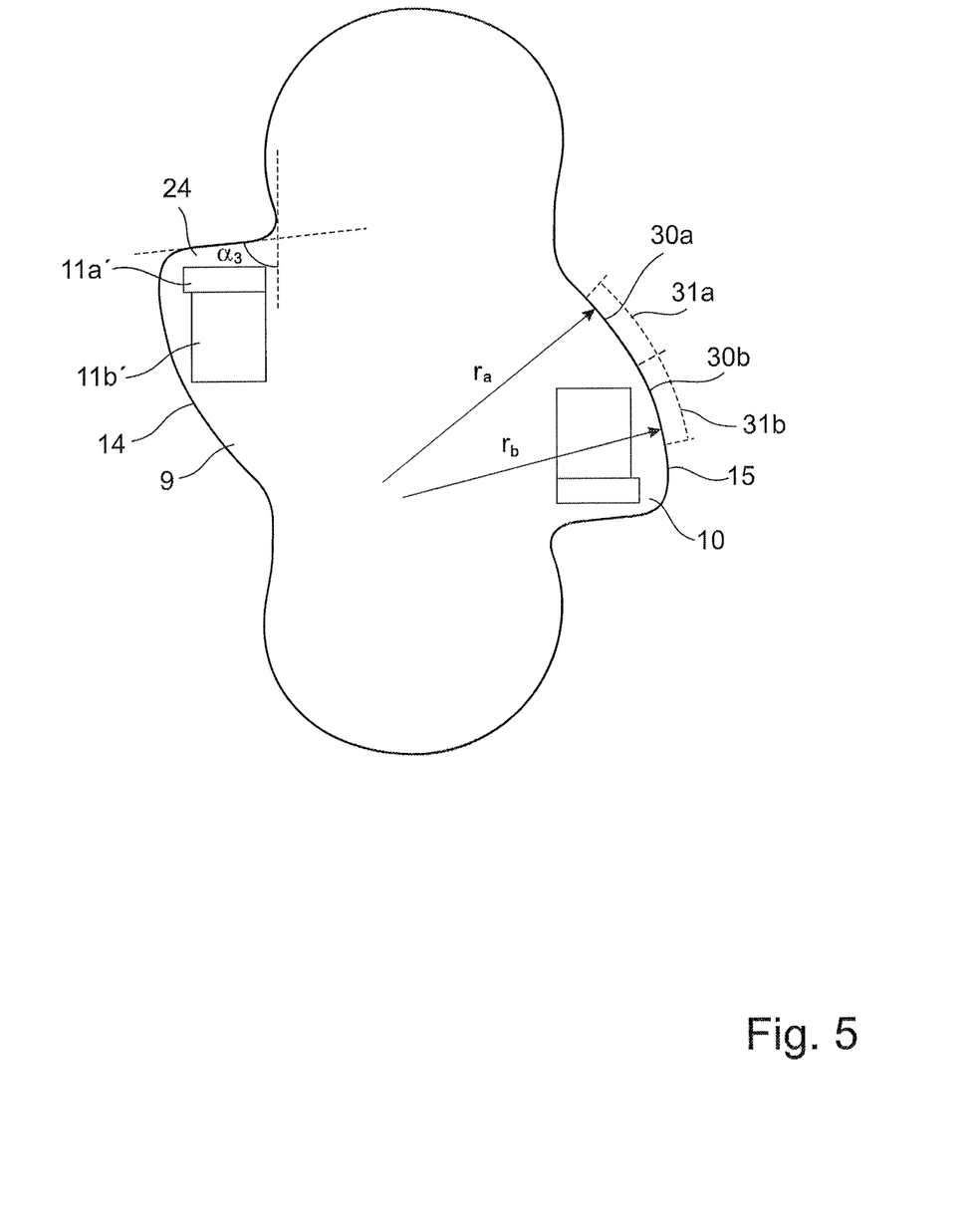
FIG. 5 shows a further embodiment of the present disclosure.

As shown in FIG. 3, the fastening means 11, 12 can be formed by a number of relatively small areas 11a, 11b or strips which together cover an area of the corresponding wing 10. These small areas 11a, 11b can be rectangular, as shown in FIG. 3, or can be of any other suitable form in order to cover a suitable area of the corresponding wing 10. As an alternative embodiment which is shown in FIG. 5, these areas 11a', 11b' can be arranged so that they extend in a direction which is transverse to the longitudinal axis Y1. Also, in a manner which is similar to FIG. 1, the areas 11a', 11b' shown in FIG. 5 are placed so that a grip tab 24 is formed next to the areas 11a', 11b'.

It should be noted that the embodiment shown in FIG. 5 is arranged so that the third angle α3 which is formed between the line 21a and the longitudinal axis Y1 (see also FIG. 1) is actually less than 90°. This is to indicate that the present disclosure is not limited to any particular magnitude of said third angle α3.

FIG. 5 also shows an embodiment of the present disclosure in which the outer edge 15 of the second wing 10 defines a first arc 30a of a circle coinciding with a first section 31a of said outer edge 14, and a second arc 30b of a circle coinciding with a second section 31b of said outer edge 14. The first arc 30a has a first radius ra, whereas the second arc 30b has a second radius rb. Consequently, this embodiment shows that the present disclosure can be formed so that the outer edge 15 comprises two or more sections with mutually different curvature. It should be noted that the first wing 9 is shaped in a corresponding manner.

According to a further embodiment, the outer edge can be shaped in a manner so that a generally straight section extends between the first arc 30a and the second arc 30b. This is not shown in the drawings.

Figure 6:
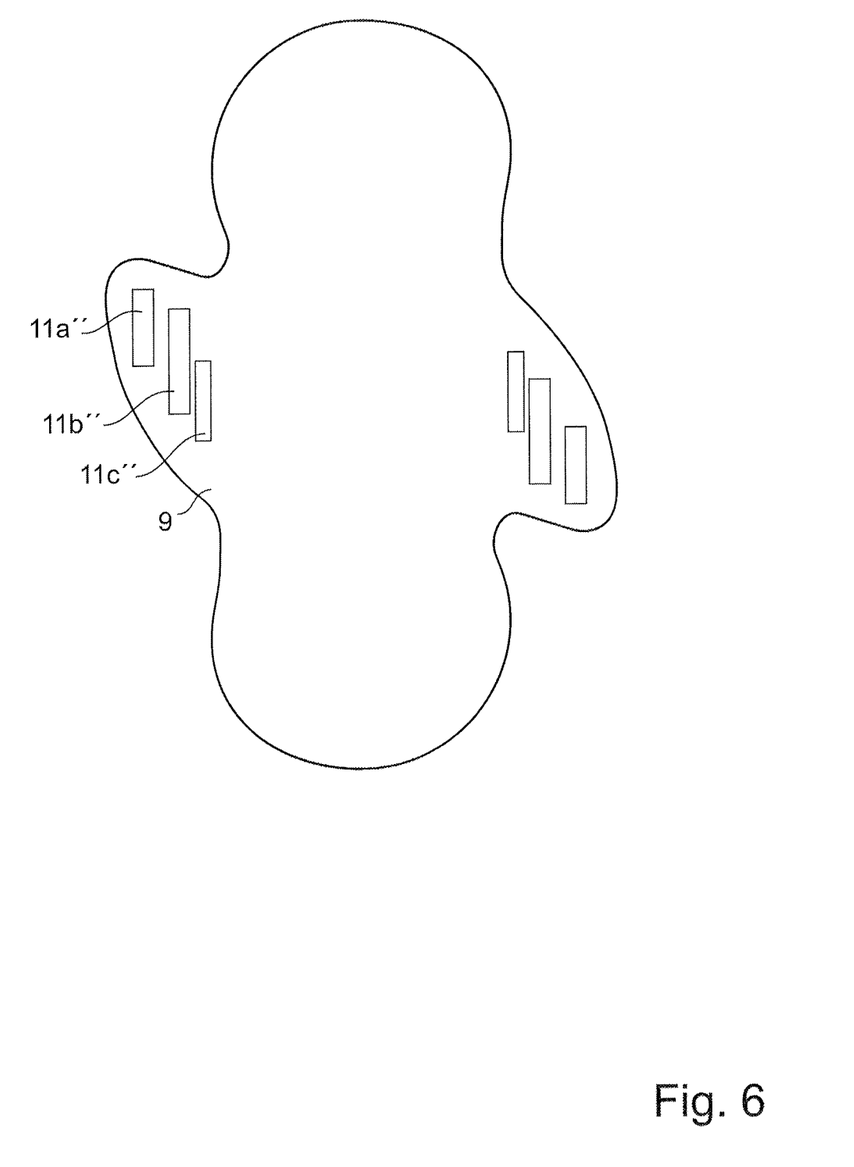
FIG. 6 shows a further embodiment of the present disclosure.

An additional embodiment is shown in FIG. 6. The purpose of this embodiment is to demonstrate that the areas 11a″, 11b″, 11c″ could be two or more in number, and could have different length and width. Also, the areas can be positioned directly adjacent to each other or be separated by a gap, as shown in FIG. 6. Also, the areas can be laid out on different positions in the article 1, as indicated in FIG. 6 showing that the transversal distance between the first area 11a″ and the second area 11b″ is greater than the transversal distance between the second area 11b″ and the third area 11c″.

A process for manufacturing the sanitary napkin 1 described above comprises a number of steps which will now be described. Initially, a material which constitutes the absorbent core 4 is sandwiched between the backsheet 2 and the topsheet 3 in a manner which is known as such. In this manner, the main body 2 is formed. Subsequently, the first wing 9 and the second wing 10 are formed in a manner so that they extend outwardly from the main body 2, in opposite directions and generally along said transversal axis X1, as described above. Furthermore, the wings 9, 10 are provided with fastening means 11, 12 for fastening the wings 9, 10 to a garment when they are folded over the main body 2. Furthermore, the manufacturing method comprises a step of arranging the first wing 9 so as to support a first fastening means (11) and arranging said second wing (10) so as to support a second fastening means (12). Also, the method comprises positioning the first and second fastening means on each wing 9, 10 in a manner so that said first and second fastening means 11, 12 are off-set from each other in the longitudinal direction.

According to an embodiment, the wings 9, 10 may be arranged so as to extend generally along a common straight line 13 which defines an angle α1 with respect to said transversal axis X1 and which exceeds 0 degrees but is less than 45 degrees.

After manufacturing of the sanitary napkin 1, it is packaged by first folding the back portion 7 and the front portion 6 over the crotch portion 8, after which the folded napkin 1 is wrapped in an individual wrapping and stored in a box. Alternatively, the front portion 6 can be folded first over the crotch portion 8, after which the back portion 7 is folded over the crotch portion 8 and the folded napkin 1 is then wrapped.

As mentioned above with reference to FIG. 3, the wings 9, 10 are folded along the first folding edge 26 during the manufacturing step. During manufacturing, however, the sanitary napkin 1 can alternatively be folded in a manner in which the wings 9, 10 and parts of the edge region 28 are folded along the core edge 27. This means that the width of the folded product can be made less than according to prior art, which is an advantage since the quantity of some of the material needed—in particular the release paper 19 and the wrapping material—can be reduced.

The present disclosure is not limited to the embodiment but can be varied within the scope of the appended claims. For example, the particular shape of the wings 9, 10 may vary within the scope of the claims. Also, the materials and dimensions used for the different layers forming the absorbent article 1 can be varied, as indicated above. Also, all embodiments of wings and other geometries can be reversed as compared with the shown embodiments.

The invention claimed is:

1. An absorbent article comprising a main body having a liquid-permeable topsheet, a liquid-impermeable backsheet and an absorbent core sandwiched between said topsheet and said backsheet, said main body being arranged along a longitudinal axis (Y1) and a transversal axis (X1) extending in a perpendicular direction in relation to the longitudinal axis (Y1), said main body defining a front portion, a back portion and a crotch portion; wherein said article comprises a first wing and a second wing extending outwardly from said crotch portion of the main body in opposite directions in an asymmetric manner with reference to the longitudinal axis (Y1), and generally along said transversal axis (X1), said wings being provided with fastening means configured for fastening said wings to a garment when being folded over said main body and towards said longitudinal axis (Y1), wherein the first wing comprises a first fastening means and the second wing comprises a second fastening means, wherein said first and second fastening means are offset from each other in the longitudinal direction of the article such that said first and second fastening means are separated by a spacing along the longitudinal direction and therefore do not overlap along any line parallel to said transversal axis (X1), and said first and second fastening means are also offset from each other in the transversal direction of the article when the wings are folded under the main body in a direction towards the longitudinal axis Y1 such that said first and second fastening means are separated by a spacing along the transversal direction and therefore do not overlap along any line parallel to said longitudinal axis (Y1).

2. The absorbent article according to claim 1, wherein each of said fastening means are positioned on opposite sides of the transversal axis (X1).

3. The absorbent article according to claim 1, wherein each of the fastening means comprises a fastening material and forms a first and second fastening area.

4. The absorbent article according to claim 3, wherein first and second fastening area defines centre point, wherein the centre point on the first fastening area is offset from the centre point on the second fastening area in the longitudinal direction of the article.

5. The absorbent article according to claim 3, wherein a position of the first fastening area does not coincide with a position of the second fastening area as mirrored along a machine direction of the article.

6. The absorbent article according to claim 1, wherein each one of said fastening means comprises an adhesive material and forms a first and second adhesive area.

7. The absorbent article according to claim 1, wherein said wings extend generally along a common straight line which defines a first angle (α1) with respect to said transversal axis (X1) which exceeds 0° but which is less than 45°.

8. The absorbent article according to claim 7, wherein the first wing is formed with an outer edge which includes a first point in the form of a transversally outermost point, and the second wing is formed with an outer edge which includes a second point in the form of a transversally outermost point, and wherein said straight line extends through the first point and the second point.

9. The absorbent article according to claim 7, wherein the first angle (α1) is within an interval of 10°-35°.

10. The absorbent article according to claim 1, wherein each wing has an outer edge which is generally straight and parallel to the longitudinal axis (Y1).

11. The absorbent article according to claim 1, wherein said fastening means is constituted by two generally rectangular strips extending in the longitudinal direction of the article.

12. The absorbent article according to claim 1, wherein said fastening means are covered, during manufacturing, by a release layer.

13. The absorbent article according to claim 1, wherein each wing defines a first straight line between a first point and a further point, and a second straight line along an upper edge section, wherein the first line defines a second angle ($\alpha 2$) with respect to the longitudinal axis (Y1) and wherein the second line defines a third angle ($\alpha 3$) with respect to the longitudinal axis (Y1), a magnitude of each angle ($\alpha 2$, $\alpha 3$) being chosen so that $\alpha 2 < \alpha 3$, or $\alpha 2 > \alpha 3$, or $\alpha 2 = \alpha 3$.

14. The absorbent article according to claim 13, wherein the magnitude of said second angle ($\alpha 2$) is chosen so that: $10° < \alpha 2 < 65°$.

15. The absorbent article according to claim 13, wherein the magnitude of said third angle ($\alpha 3$) is chosen so that: $60° < \alpha 3 < 120°$.

16. The absorbent article according to claim 1, wherein said wings are formed with an area between said fastening means and a further edge which constitutes a grip tab.

17. The absorbent article according claim 1, wherein a first distance (d1), as defined between an outer edge of each wing and the longitudinal axis (Y1), is in a range of 40-100 mm.

18. The absorbent article according to claim 1, wherein a second wing folding edge is defined where each wing can be folded during use of the article, said second wing folding edge having a length which is within an interval of 10-80% of a full length of the main body.

19. The absorbent article according to claim 1, wherein each longitudinal side of the absorbent core at least partly defines a core edge which is generally parallel to the longitudinal axis (Y1).

20. The absorbent article according to claim 1, wherein the absorbent core generally follows an outer edge of the main body and defines an edge region of the main body which is generally equally wide along an entire periphery of the absorbent core.

21. The absorbent article according to claim 1, wherein the article comprises a further fastening means positioned along the main body on a garment-facing side of said backsheet.

22. The absorbent article according to claim 1, wherein the first and second wings are at least partially overlapping along the longitudinal direction of the article, such overlap being located away from locations of the first and second fastening means, which remain offset from each other in the longitudinal direction.

23. A method for manufacturing an absorbent article having a longitudinal extension along a longitudinal axis (Y1) and a transversal extension along a transversal axis (X1), said article defining a front portion, a back portion and a crotch region, said method comprising forming a main body by providing a liquid-permeable topsheet, providing a liquid-impermeable backsheet and sandwiching an absorbent body between said topsheet and said backsheet; forming a first wing and a second wing configured so as to extend outwardly from said main body in opposite directions in an asymmetric manner with reference to the longitudinal axis (Y1) and generally along said transversal axis (X1); and providing said wings with fastening means for fastening said wings to a garment when being folded over said main body and towards said longitudinal axis (Y1); arranging said first wing so as to support a first fastening means; arranging said second wing (10) so as to support a second fastening means; and positioning said first and second fastening means on each wing in a manner so that said first and second fastening means are offset from each other in the longitudinal direction of the article such that said first and second fastening means are separated by a spacing along the longitudinal direction and therefore do not overlap along any line parallel to said transversal axis (X1), and also so that said first and second fastening means are also offset from each other in the transversal direction of the article when the wings are folded under the main body in a direction towards the longitudinal axis (Y1) such that said first and second fastening means are separated by a spacing along the transversal direction and therefore do not overlap along any line parallel to said longitudinal axis (Y1).

* * * * *